United States Patent
Hardy et al.

(10) Patent No.: US 10,933,160 B2
(45) Date of Patent: **\*Mar. 2, 2021**

(54) DEGRADABLE HAEMOSTAT COMPOSITION

(71) Applicant: Medtrade Products Limited, Crewe (GB)

(72) Inventors: Craig Hardy, Cardigan (GB); Andrew Hoggarth, Crewe (GB); June Gladman, Warrington (GB)

(73) Assignee: MEDTRADE PRODUCTS LIMITED, Crewe (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,475

(22) PCT Filed: May 28, 2014

(86) PCT No.: PCT/GB2014/051624
§ 371 (c)(1),
(2) Date: Nov. 27, 2015

(87) PCT Pub. No.: WO2014/191738
PCT Pub. Date: Dec. 4, 2014

(65) Prior Publication Data
US 2016/0106882 A1    Apr. 21, 2016

(30) Foreign Application Priority Data

May 30, 2013    (GB) ..................................... 1309674

(51) Int. Cl.
| | |
|---|---|
| *A61L 24/08* | (2006.01) |
| *A61L 24/00* | (2006.01) |
| *A61L 15/28* | (2006.01) |
| *A61L 15/64* | (2006.01) |
| *A61K 31/722* | (2006.01) |
| *A61P 7/04* | (2006.01) |
| *C08B 37/00* | (2006.01) |
| *C08L 5/08* | (2006.01) |
| *C08B 37/08* | (2006.01) |

(52) U.S. Cl.
CPC ............ *A61L 24/08* (2013.01); *A61K 31/722* (2013.01); *A61L 15/28* (2013.01); *A61L 15/64* (2013.01); *A61L 24/0042* (2013.01); *A61P 7/04* (2018.01); *C08B 37/003* (2013.01); *A61L 2400/04* (2013.01)

(58) Field of Classification Search
CPC .. A61L 24/08; A61L 2400/04; A61L 24/0042; A61L 15/28; A61L 15/64; C08B 37/003; C08L 5/08; A61P 7/04; A61K 31/722
See application file for complete search history.

(56) References Cited

U.S. PATENT DOCUMENTS

| | | | | |
|---|---|---|---|---|
| 4,394,373 | A | * | 7/1983 | Malette ................ A61K 31/715 514/55 |
| 5,578,661 | A | * | 11/1996 | Fox ........................ C08L 71/02 524/27 |
| 2005/0080245 | A1 | * | 4/2005 | Hung ................... A61K 31/722 536/20 |
| 2005/0240137 | A1 | | 10/2005 | Zhu et al. |
| 2008/0248508 | A1 | | 10/2008 | Baker et al. |
| 2009/0062849 | A1 | * | 3/2009 | Dowling ............ A61K 47/4823 606/214 |
| 2011/0236433 | A1 | * | 9/2011 | Hardy ..................... A61L 15/60 424/400 |

FOREIGN PATENT DOCUMENTS

| | | | |
|---|---|---|---|
| CN | 101601643 A | * | 12/2009 |
| EP | 0 424 672 A1 | | 5/1991 |
| EP | 1 859 816 A1 | | 11/2007 |
| GB | 201205174 | * | 5/2012 .......... A61L 26/009 |
| JP | 06-263799 A | | 9/1994 |
| WO | 02102276 | | 12/2002 |
| WO | 2005/034865 A2 | | 4/2005 |
| WO | 2005087280 | | 9/2005 |
| WO | 2006/134614 A1 | | 12/2006 |
| WO | 2007074326 | | 7/2007 |
| WO | 2008/063503 A2 | | 5/2008 |
| WO | WO-2008063503 A2 | * | 5/2008 ......... C08B 37/0003 |
| WO | 2009130485 | | 10/2009 |
| WO | 2010/107794 A2 | | 9/2010 |
| WO | 2012123728 | | 9/2012 |
| WO | 2013/140190 A1 | | 9/2013 |

OTHER PUBLICATIONS

Google English translation of Yan (CN101601643A) (Dec. 16, 2009).*
Wg et al., "Chitosan: a new hemostatic", Ann Thorac Surg, Jul. 1983: 36(1):55-8.*
International Search Report to corresponding international patent appl. No. PCT/GB2014/051624, dated Sep. 25, 2014, 3 pages.

* cited by examiner

*Primary Examiner* — Kyung S Chang
(74) *Attorney, Agent, or Firm* — Tarolli, Sundheim, Covell & Tummino LLP

(57) ABSTRACT

In one aspect, the present invention includes a haemostat composition that has been washed with an alkali solution to reduce the presence of endotoxins, and which is able to safely gradually and fully degrade in a human or animal body within about 30 days and so can be utilised by physicians to stem a flow of blood and promote healing both after as well as during surgical procedures.

25 Claims, No Drawings

DEGRADABLE HAEMOSTAT COMPOSITION

CROSS-REFERENCE TO RELATED APPLICATIONS

This application is the U.S. national phase entry of PCT/GB2014/051624, with an international filing date of May 28, 2014, which claims priority to and the benefit of GB 1309674.8, filed on May 30, 2013, the contents of which are hereby incorporated by reference in their entirety.

TECHNICAL FIELD

The present invention relates to a haemostat composition that is capable of safely gradually and completely degrading within the body of a human or animal, and can therefore be utilised by physicians to stem a flow of blood and promote healing both after as well as during surgical procedures.

BACKGROUND

Haemostat materials for use in the treatment of wounds or other openings at a physiological target site in or on human or animal body which are exuding blood and/or other bodily fluids have been known for some time. These haemostat materials act to absorb the blood and/or other bodily fluids, and also stem the flow of them from the body. Haemostat materials for such use are described in, for example, WO 2009/130485 and WO 2012/123728 to MedTrade Products Ltd., and are commercially available under the trade name Celox®.

One material that is commonly employed as a haemostat material is chitosan. Chitosan is a known haemostat material, and is a derivative of solid waste from shellfish processing and can be extracted from fungus culture. It is a cationic polymeric material that is insoluble in water.

There are many different types of chitosan that may be used as a haemostat material, with different haemostatic properties. The different types of chitosan may have different molecular weights, different degrees of deacetylation, different arrangements of the two monomers, different chiral forms, or they may be derived from different species or sources (and fungi), or may have been treated differently during manufacture. Each of these differences can impact upon the levels of solubility and polymer structures of the respective chitosan materials, and therefore provide different chitosan materials having differing haemostatic properties.

The control of bleeding is essential and critical during surgical procedures. The aim of controlling bleeding is essentially to minimize blood loss, which in turn may shorten the duration of the surgery in the operating room and ultimately lead to a reduction in post-surgical complications. Haemostat compositions are of significant use during surgery for this purpose, but must always be removed at the end of the procedure when the incision in the patient is closed up.

However, there remains a need for a haemostat composition that is able to be used safely within the human or animal body, after as well as during surgical procedures, and which can subsequently be allowed to remain in the body to promote healing post-surgery. It would be beneficial to have a haemostat composition that is safely absorbable within the body within a defined period of time, as this would eliminate the need to remove the product prior to closure of the patient, and would allow the haemostat composition to remain in the body to reduce the likelihood for re-bleeding post-surgery. Further, such an absorbable and degradable haemostat composition would negate the need for further surgery to remove the haemostat. Such a degradable haemostat composition for post-surgical use has never previously been developed.

SUMMARY

Therefore, in accordance with the invention, there is provided a haemostat composition comprising a chitosan, chitosan salt or chitosan derivative, wherein the haemostat composition is in non-fibrous form, and is able to fully degrade in a human or animal body within about 30 days.

By "haemostat", it is meant herein any agent which is capable of producing a clot or plug which stops or reduces bleeding when it comes into contact with blood or other bodily fluid.

By the term 'chitosan derivative' is meant herein a partially deacetylated chitin, which may have different percentages of deacetylation, as desired. Typically, the partially deacetylated chitin suitable for use in the present invention has a deacetylation degree above about 50%, more typically above about 75% and most typically above about 85%.

Also herein included within the term 'chitosan derivative' are reaction products of chitosan with other compounds. Such reaction products include, but are not limited to, carboxy methyl chitosan, hydroxyl butyl chitin, N-acyl chitosan, O-acyl chitosan, N-alkyl chitosan, O-alkyl chitosan, N-alkylidene chitosan, O-sulfonyl chitosan, sulfated chitosan, phosphorylated chitosan, nitrated chitosan, alkalichitin, alkalichitosan, or metal chelates with chitosan, etc.

Suitable non-fibrous forms for the haemostat composition of the invention include, but are not limited to, granules, powder, a sheet, a foam, a freeze dried foam, a compressed foam, a film, a perforated film, beads, a gel, a hydrogel (sheets and amorphous), or a laminate, or a combination of any two or more thereof.

By 'sheet' is meant an aqueous form of the chitosan, chitosan salt or chitosan derivative that has been dried into a sheet of a physiologically acceptable degradable material.

The haemostat composition of the invention will typically be completely degraded within the human or animal body between about 1 to no more than about 30 days after its introduction into the body, more typically within this range after about 4 days, still more typically within this range after about 7 or about 10 days. As the haemostat composition will typically not be completely degraded within about 24 hours, more typically not within about 4 days, or even within about 7 days, this permits the haemostat composition to remain in the human or animal body for a sufficient period of time after the surgical procedure or closing of a wound, so that it may aid in preventing or reducing any incidence of re-bleeding at the physiological target site, and also aid in the healing process. Too rapid a degradation could potentially lead to late re-bleeds and would limit the effectiveness of the haemostat composition in aiding in the post-surgery healing process. For example, the haemostat composition may be still be present in the body about 7 days after the surgical procedure or closing of a wound, but will have subsequently completely degraded after 30 days.

The haemostat composition of the invention will typically also contain a physiologically acceptable acid. The amount of acid relative to the chitosan, chitosan salt or chitosan derivative has an effect on the degradation properties of the haemostat composition of the invention. Typically, if the amount of acid in the haemostat composition is at about 20% or less by weight of the haemostat composition, such as in WO 2009/130485 to MedTrade Products Ltd, the degradation time is greater than 30 days. A degradation period above 30 days would mean that the product of the invention would fall into a different medical regulatory and safety category. Conversely, if the ratio of acid is greater than about 70% by weight of the haemostat composition, the haemostat composition typically dissolves too rapidly upon contact with blood, loses its gelling properties, and because it degrades too quickly, it also loses its ability to be an effective haemostat.

The chitosan, chitosan salt or a chitosan derivative used in the present invention does not need to be subjected to any heat treatment, other than optionally in the removal of any solvents to dry the composition, which is typically done at temperatures of no more than 40° C. No heat treatment is necessary after the composition has been dried. This is because subjecting the composition to heat treatment would impart undesirable increased insolubility and cohesion properties upon the haemostat composition, which would result in the haemostat composition having reduced degradation properties, leading to it being unable to degrade sufficiently in the body within 30 days.

According to another embodiment of the invention, the haemostat composition will typically have an absorption of less than about 20 g/g, more typically less than about 15 g/g. By an absorption of less than about 20 g/g is meant that the haemostat composition will absorb less than 20 g of fluid per gram of the composition, typically about 15-18 g/g.

The haemostat composition of the invention works effectively at normal body temperatures (37° C.).

According to one embodiment of the invention, the haemostat composition may be blended with other physiologically safe materials, such as, for example, oxidised cellulose or collagen, etc. Other suitable and safely degradable materials that may be combined with the haemostat composition will be apparent to the person skilled in the art.

According to one embodiment of the invention, the haemostat composition consists of a chitosan, chitosan salt or chitosan derivative together with a physiologically acceptable acid. In this embodiment, no carrier material is used for the composition.

The physiologically acceptable acid is typically present in an amount of more than about 20% and below about 70% by weight of the haemostat composition, more typically more than about 25% by weight of the haemostat composition to about 65%, more typically from about 30% to about 60% by weight of the haemostat composition, more typically from about 35% to about 55% by weight of the haemostat composition. However, amounts of acid of about 35%, 40%, 45%, and 50% are also envisaged within the scope of the invention.

For example, if chitosan is in the form of granules, then an amount of acid, such as lactic acid, between about 45-65% by weight of the haemostat composition, more typically between about 50-60% by weight of the haemostat composition may be used, most typically between about 53-57% by weight of the haemostat composition. It will be appreciated that the optimum amount of acid for the desired degradation properties may vary with different acids, and also with different grades of chitosan. The optimum amount of acid required for the desired degradation properties may differ depending upon the form of the chitosan haemostat, among other factors.

It will be appreciated that the optimum amount of acid for a desired rate of degradation may vary with different carboxylic acids, with different amounts of the acid, and also with the different grades and types of chitosan detailed above.

Examples of acids that may be used include, but are not limited to, organic acids and/or inorganic acids, including carboxylic acids, monovalent, divalent or multivalent acids. Non-limiting examples of carboxylic acids include formic acid, acetic acid, ascorbic acid, halogen acetic acids (such as fluoro- or chloroacetic acid), propanoic acid, propenoic acid, lactic acid, succinic acid, acrylic acid, glyoxylic acid, pyruvic acid or a hydroxy propionic/butanoic acid, or combinations of any two or more thereof. More typically, the carboxylic acids used are one or more acids selected from lactic, acetic and succinic acids. Most typically, the carboxylic acid used comprises lactic and/or acetic acids, especially lactic acid. Non-limiting examples of inorganic acids include one or more selected from hydrochloric acid and sulphuric acid. The use of an acid which is already present in the human or animal body is advantageous in facilitating the bioacceptability of the haemostat composition as it degrades.

As discussed above, the amount of acid that is present in the haemostat composition can significantly impact upon the degradation properties of the composition, and may also be determined by the form of the composition that is to be used.

According to another embodiment of the invention, the haemostat composition comprises a chitosan salt and the physiologically acceptable acid is a carboxylic acid, such as lactic acid, while the haemostat composition is in the form of granules or powder.

According to another embodiment of the invention, the haemostat composition comprises a chitosan salt, the physiologically acceptable acid is a carboxylic acid, such as lactic acid, and the acid is present in an amount of between about 45-60% by weight of the haemostat composition, more typically between about 50-55% by weight of the haemostat composition, and the haemostat composition is in the form of granules or powder.

According to one embodiment of the invention, the haemostat composition is a chitosan salt. If a chitosan salt is used, the salt is typically prepared in situ when the chitosan comes into contact with an appropriate acid. It will be appreciated that the acid may be any inorganic or organic acid which yields a chitosan salt that is soluble in bodily fluids and that can be safely degraded within the human or animal body. The appropriate acids or combination of acids for yielding a soluble chitosan salt will be apparent to a skilled person. For example, chitosan phosphate is substantially insoluble in water, and so use of phosphoric acid alone would hence be less suitable as the acid for this purpose. Typical chitosan salts include herein, but are not limited to, one or more salts selected from chitosan acetate, chitosan lactate, chitosan succinate, chitosan malate, chitosan acrylate, chitosan formate, chitosan ascorbate, chitosan fluoroacetate, chitosan chloroacetate, chitosan propanoate, chitosan glyoxylate, chitosan pyruvate, chitosan sulphate, or chitosan chloride. More typically, the chitosan salt used in the present invention is chitosan lactate.

Chitosan can act as a haemostat in two ways; either by gelling with water in the blood and bonding to wet tissue to plug a wound, or by dissolving and bonding with the surface of red blood cells to create a clot-like gel. The properties of the combinations of chitosan and acid are dependent upon the precise nature of the chitosan (e.g. molecular weight and degree of deacetylation), as well as the particular acid used and the quantities present.

Chitosan salts are ideally suited for the applications described herein as chitosan is readily broken down in the body. Chitosan is converted to glucosamine by the enzyme lysozyme and is therefore excreted from the body naturally. It is not necessary to take any measures to remove the chitosan from the body.

Furthermore, chitosan salts exhibit mild antibacterial properties and as such their use reduces the risk of infection.

Typically, the molecular weight of the chitosan used for the preparation of the haemostat composition according to the present invention is less than about 2,000,000, more typically less than about 1,000,000, and even more typically less than about 500,000, and most typically less than about 175,000.

The viscosity of the chitosan used according to the invention may typically be less than about 1000 cps, more typically less than about 500, even more typically less than about 300. Advantageously, the viscosity is from about 40 to about 200 cps when measured on a Brookfield viscometer at 20° C.

The chitosan typically has a pH of from about 6.0 to about 8.0. Chitosan salts can have a pH from about 3.5 to about 8.0. The pH is largely dependent upon the particular chitosan or chitosan salt used, as they each have a different pH.

The chitosan material may be provided in a sterile or non-sterile form. Where the material is initially provided in a non-sterile form, sterilisation may be carried out using any of the known methods, such as gamma irradiation, electron beam treatment, heat treatment, etc, or by treatment using ethylene oxide. A material in a non-sterile four may be provided in combination with one or more preservatives. However, for a greater ease of use for a physician, it is preferred that the haemostat composition is provided in a pre-sterilised form.

According to one embodiment, if the haemostat is in particulate or granular form, at least about 50% of the particles or granules have an average particle size of greater than about 250 microns (60 mesh), while about 20% to about 30% of the particles have an average particle size of less than about 250 microns. Typically, almost all of the particles, such as about 99% thereof, have an average particle size of less than about 2000 microns (10 mesh), with less than about 1%—and ideally 0%—having an average particle size greater than about 2000 microns. Also, about 5% of the particles have an average particle size greater than about 1000 microns. By 'particle size' is meant herein the size of a granule between its furthest points, and the 'average particle size' represents the average of all of the particle sizes in a batch of granules in the haemostat composition.

If the haemostat composition is in the form of a sheet or film, then it may take any suitable form and may be provided in a range of different sizes, shapes and thicknesses necessary to deal with a physiological target site, such as square, rectangular, circular or elliptical. The physiological target sites to be treated may be of differing sizes and shapes. For example, the sheet or film may be a generally flat shape with little height relative to its width/depth. Any regular or irregular shape may be employed. It may also be provided in larger dimensions which can then be cut to the required size.

The thickness of the sheet or film may be varied between upper and lower limits as desired. The upper limit of the thickness is typically about 5 cm, down to a few microns, such as 5-10 microns. It is however important that the sheet or film is flexible so that it can be curved to fit the contours of the physiological target sites to be treated, if necessary. Typically, the thickness is from about 1.5 mm to about 3.0 mm.

In accordance with the invention, it is possible to control the rate of degradation of the haemostat composition by selecting particular combinations of chitosan properties, such as molecular weight or viscosity, or selecting a particular chitosan salt, as well as by varying the amount of acid component.

Of course, in order that the haemostat composition of the invention is able to be safely inserted into the human or animal body, it must be entirely physiologically acceptable, and only contain components that are not harmful to the human or animal body.

The physiological target site may be any site in the body of an animal that is exposed during a surgical procedure. The animal may be a human or a non-human animal.

The haemostatic composition described herein provides and maintains effective haemostasis when applied to a wound requiring haemostasis. Effective haemostasis, as used herein, is the ability to control and/or abate capillary, venous, or arteriole bleeding within an effective time, as recognized by those skilled in the art of haemostasis.

In certain embodiments, the haemostatic composition of the present invention is effective in providing and maintaining haemostasis in cases of severe or brisk bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as haemophilia.

The haemostatic composition herein also provides and maintains effective haemostasis when applied to a wound whereby the patient and/or person requiring haemostasis are on anti-coagulant therapy, for example, heparin and warfarin.

In surgical procedures whereby haemostasis may be critical to survival of the patient, it is therefore desirable to have a haemostatic composition that does not require preparation and that is ready for use upon removal from its packaging. The haemostatic composition of the invention fulfils this requirement. Also, the haemostatic composition of the invention is capable of being applied on either surface thereof, reducing the risk of incorrect application.

It is also beneficial to deliver a haemostat composition that is able to adhere to the body tissues, ensuring that any haemostat product is not removed due to movement and stays in place until it is fully absorbed by the body, reducing the risk of re-bleeding. The haemostatic composition of the invention has a known metabolic pathway, via the known conversion of chitosan to glucosamine by the lysozyme, so the body can dispose of it in a safe manner.

Further components which may be added to the haemostat composition include, but are not limited to, one or more selected from pharmaceutical agents; wetting agents such as surfactants; growth factors; cytokines; agents which absorb agents which delay healing such as MMP's (matrix metalloproteinases) and elastase; and/or another haemostat component, such as calcium, vitamin K, fibrinogen, thrombin, factor VII, factor VIII, clays such as kaolin, oxidised regenerated cellulose, gelatin, or collagen, etc.

Typical levels of any of these components could be from about 50 ppm levels up to about 50% by weight of the haemostat composition. More typical levels would be less than about 10%, still more typically less than about 5%, by weight of the haemostat composition. Less than about 1% by weight of the haemostat composition of these components is also envisaged within the invention.

In order to evaluate the degradation properties of the haemostat composition, the composition has been tested in solutions which closely replicate the conditions within the human or animal body in which it would be used. As such, the haemostat composition of the invention has been shown to degrade in lysozyme solution, serum and simulated wound fluid. The simulated wound fluid contains 50% Fetal Bovine Serum and 50% Peptone water (0.9% NaCl+0.1% peptone in de-ionised $H_2O$).

Firstly, the haemostat composition of the invention is immersed in a solution of each of lysozyme solution, serum and simulated wound fluid. In each case, the volume of the solution is greater than maximum absorbency of the composition.

The haemostat composition and the solution is then sealed and incubated at 37° C.—i.e. body temperature—for a period of up to 30 days.

During this period, the degradation of the composition is visually assessed at numerous time points to determine whether the composition has completely degraded.

According to a further aspect of the invention, there is provided a method of manufacturing a haemostat composition comprising a chitosan, chitosan salt or chitosan derivative, wherein the haemostat composition is in a non-fibrous form, and is able to fully degrade in a human or animal body within about 30 days. The method may comprise coating the chitosan, chitosan salt or chitosan derivative with a physiologically acceptable acid.

The acid used may be any of those listed herein above, and in any of the amounts as detailed above. The acid is typically lactic acid, but is not limited thereto. Once the chitosan, chitosan salt or chitosan derivative has been coated by the acid, it is dried.

In one embodiment, the chitosan raw material may first be washed to reduce the presence of endotoxins prior to the coating step. This may be carried out using contacting the chitosan, chitosan salt or chitosan derivative with an alkali solution to form a mixture, and then leaving the mixture for a period of time, which may be as short as about 1 minute to longer than about 12 hours, before finally drying the mixture. By 'alkali solution' is meant a solution having a pH value of greater than pH 7.5.

The concentration of alkali solution used in the process may be from about 0.01M to about 1M. Typically, the concentration of alkali solution is from about 0.02M to about 0.2M, more typically about 0.1M.

The quantity of alkali solution to chitosan may be in the range of from about 1 part chitosan to about 10 parts alkali solution up to about 10 parts chitosan to about 1 part alkali solution. Typically, the quantity of alkali solution to chitosan is about 1 part alkali solution to about 2 parts chitosan, more typically about 1 part alkali solution to about 1 part chitosan.

The alkali solution may comprise an alkali or alkaline earth component selected from the following, either alone or in combination: metal hydroxides, metal carbonates, metal bisulphites, metal persilicates, conjugate bases and ammonium hydroxide.

Suitable metals include sodium, potassium, calcium, or magnesium. Typically, the alkali component is sodium hydroxide, potassium hydroxide or sodium carbonate. Typically, sodium hydroxide is used.

Additionally, the haemostat composition of the invention may be first washed to reduce the presence of endotoxins as described above. Typically, this washing step is carried out.

Subsequently, the chitosan, chitosan salt or chitosan derivative is then processed to form the final product. By way of a typical but non-limiting example where the haemostat composition according to the invention is in granular or powder form, granules are washed with the alkali solution and dried. The physiologically acceptable acid is then applied to the washed granules, which are dried and then milled to particles having the desired average particle size, which are then presented in applicators or pouches. Alternatively, where the haemostat composition is in the form of e.g. a sheet or film, once the sheet or film has had the physiologically acceptable acid applied to it, it is then dried, before finally being cut into pieces of the desired sizes.

In each embodiment, the haemostat composition is typically also sterilised prior to being packaged, in order that a physician can use the composition directly from its packaging.

The present invention also provides a method of absorbing a discharge of a fluid, such as blood, and a method of stemming a flow of a fluid such as blood from a physiological target site, comprising applying to the target site a haemostat composition as described herein.

According to a further aspect of the invention, there is provided a use of a haemostat composition as described herein in absorbing a discharge of a bodily fluid from a physiological target site, or of stemming a flow of a fluid discharged from a physiological target site.

When the haemostat composition of the invention is used in absorbing a discharge of a fluid, or in stemming a flow of a fluid such as blood from a physiological target site, it is typically retained within a human or animal body after a medical procedure in order to provide post-surgical haemostasis, to reduce the likelihood for re-bleeding post-surgery and to promote post-surgical healing.

DETAILED DESCRIPTION

The invention will now be described further by way of example with reference to the following examples which are intended to be illustrative only and in no way limiting upon the scope of the invention.

EXAMPLES

Method

The total absorbency of the haemostat composition of the invention is determined using simulated wound fluid, serum and lysozyme solution. This is undertaken by determining the maximum absorbency of the materials by slowly adding fluid to the materials until no more can be absorbed. The amount of fluid absorbed is calculated from the wet weight minus the dry weight.

Using the total absorbency volume for the material to be tested, this volume of lysozyme solution, simulated wound fluid or serum is decanted into a clean sealable beaker.

The haemostat composition is added into the solution (the solution volume being greater than the maximum absorbency of the haemostat composition), ensuring that the weight of product is not greater than the absorbency potential for the volume of fluid within the beaker.

The haemostat composition and solution are sealed and incubated at 37° C. (i.e. body temperature) for up to 30 days.

At each time point the solution is visually assessed to determine whether and to what degree the haemostat composition has degraded.

It is to be noted that at maximum absorbency at day 1, the degradation time is quicker than if the same volume of solution is applied gradually over a 5 day period.

The haemostat composition is considered to have completely degraded if the viscosity of the lysozyme solution, simulated wound fluid or serum falls below 10 cps as measured at 20° C. on a Brookfield viscometer, measured by setting the viscometer to spindle 62 and setting the spindle speed to 60 rpm, or if the fluid in the beaker becomes optically clear with no particles or insoluble matter visible to the human eye.

The degradation data after 1 day and 5 days is provided in Tables 1 and 2.

TABLE 1

Test Data at maximum absorbency at day 1
Testing/Examples

| Sample | Days to full degradation | |
|---|---|---|
| | SWF | Lysozyme soln |
| Hemcon gauze | >30 days | >30 days |
| CG 1600 chitosan | >30 days | >30 days |
| Carboxymethylated chitosan | >30 days | >30 days |
| Chitosan/Viscose/Acid blend | >30 days | >30 days |
| Celox (chitosan salt) | >30 days | >30 days |
| Celox gauze | >30 days | >30 days |
| Chitosan granules with 20% Acid | >30 days | >30 days |
| Chitosan granules with 55% Acid | 1 day | 1 day |

TABLE 2

Test Data at maximum absorbency at day 5
(gradually added fluid over 5 days)
Testing/Examples

| Sample | Days to full degradation | |
|---|---|---|
| | SWF | Lysozyme soln |
| Hemcon gauze | >30 days | >30 days |
| CG 1600 chitosan | >30 days | >30 days |
| Carboxymethylated chitosan | >30 days | >30 days |
| Chitosan/Viscose/Acid blend | >30 days | >30 days |
| Celox (chitosan salt) | >30 days | >30 days |
| Celox gauze | >30 days | >30 days |
| Chitosan granules with 20% Acid | >30 days | >30 days |
| Chitosan granules with 55% Acid | 5 day | 5 day |

It can therefore be seen that the haemostat compositions according to the invention degrade effectively over a desired period of between 1 and 30 days in conditions designed to replicate those that would be encountered in the human or animal body, and would be able to safely remain in the human or animal body post-surgery to aid in reducing and preventing incidences of re-bleeding and promoting healing, before completely degrading and being excreted from the body naturally.

It is of course to be understood that the present invention is not intended to be restricted to the foregoing examples which are described by way of example only.

The invention claimed is:

1. A haemostat composition comprising a chitosan, chitosan salt or chitosan derivative and a physiologically acceptable acid, wherein the physiologically acceptable acid is present in an amount of between about 20% and about 70% by weight of the haemostat composition, wherein the chitosan, chitosan salt or chitosan derivative is coated by the acid, wherein the haemostat composition is in a non-fibrous form, is able to fully degrade in a human or animal body within about 30 days, and the chitosan, chitosan salt or chitosan derivative has been washed with an alkali solution prior to coating with the acid for a period of longer than about 12 hours to reduce the presence of endotoxins; wherein the alkali solution has a concentration of 0.02 M to 0.2M.

2. The haemostat composition according to claim 1, wherein the haemostat composition is in the form of granules, powder, a sheet, a foam, a freeze dried foam, a compressed foam, a film, a perforated film, beads, a gel, a hydrogel sheets and amorphous hydrogel, or a laminate, or a combination of any two or more thereof.

3. The haemostat composition according to claim 1, wherein the haemostat composition is still present in the human or animal body after about 24 hours.

4. The haemostat composition according to claim 3, wherein complete degradation of the haemostat composition occurs after more than about 4 days but less than about 30 days.

5. The haemostat composition according to claim 4, wherein complete degradation of the haemostat composition occurs after more than about 7 days but less than about 30 days.

6. The haemostat composition according to claim 1, wherein the physiologically acceptable acid is present in an amount of between about 30% and about 60% by weight of the haemostat composition.

7. The haemostat composition according to claim 6, wherein the physiologically acceptable acid is present in an amount of between about 35% and about 55% by weight of the haemostat composition.

8. The haemostat composition according to claim 1, wherein the physiologically acceptable acid comprises an organic acid and/or an inorganic acid.

9. The haemostat composition according to claim 8, wherein the organic acid comprises a carboxylic acid.

10. The haemostat composition according to claim 9, wherein the carboxylic acid is selected from formic acid, acetic acid, ascorbic acid, halogen acetic acids, propanoic acid, propenoic acid, lactic acid, succinic acid, acrylic acid, glyoxylic acid, pyruvic acid or a hydroxy propionic/butanoic acid, or combinations of any two or more thereof.

11. The haemostat composition according to claim 10, wherein the carboxylic acid is selected from lactic, acetic and succinic acids, or combinations of any two or more thereof.

12. The haemostat composition according to claim 11, wherein the carboxylic acid is lactic acid.

13. The haemostat composition according to claim 8, wherein the inorganic acid comprises one or more of hydrochloric acid and/or sulphuric acid.

14. The haemostat composition according to claim 1, wherein the haemostat composition comprises a chitosan salt.

15. The haemostat composition according to claim 14, wherein the chitosan salt comprises one or more salts selected from chitosan acetate, chitosan lactate, chitosan succinate, chitosan malate, chitosan acrylate, chitosan formate, chitosan ascorbate, chitosan fluoroacetate, chitosan chloroacetate, chitosan propanoate, chitosan glyoxylate, chitosan pyruvate, chitosan sulphate, or chitosan chloride.

16. The haemostat composition according to claim 15, wherein the chitosan salt comprises chitosan lactate.

17. The haemostat composition according to claim 1, wherein the haemostat composition comprises a chitosan salt, the physiologically acceptable acid is a carboxylic acid and is in an amount of between about 45-60% by weight of the haemostat composition, and the haemostat composition is in the form of granules or powder.

18. The haemostat composition according to claim 1, wherein the haemostat composition is made without subjecting the composition to any heat treatment after the composition has been dried.

19. The haemostat composition according to claim 1, wherein a molecular weight of the chitosan used for the preparation of the haemostat composition is less than about 500,000.

20. The haemostat composition according to claim 1, wherein a viscosity of the chitosan used for the preparation of the haemostat composition is from about 40 to about 200 cps when measured at 20° C.

21. The haemostat composition according to claim 1, wherein the haemostat composition is sterilised.

22. The haemostat composition according to claim 1, further comprising one or more components selected from pharmaceutical agents; wetting agents; colouring agents; processing aids; bulking agents; absorbent polymers; antimicrobial agents; growth factors; cytokines; agents which absorb agents which delay healing; calcium; vitamin K; fibrinogen; thrombin; factor VII; factor VIII; clays; oxidised regenerated cellulose; gelatine; and/or collagen.

23. A method of absorbing fluid discharged from a physiological target site, or of stemming a flow of a fluid discharged from a physiological target site, comprising applying to the physiological target site the haemostat according to claim 1.

24. The haemostat composition according to claim 1, wherein the haemostat composition is sterilised prior to being packaged.

25. The haemostat composition according to claim 1, wherein the chitosan derivative is a reaction product of chitosan with one or more compounds selected from the group consisting of carboxy methyl chitosan, hydroxyl butyl chitin, N-acyl chitosan, O-acyl chitosan, N-alkyl chitosan, O-alkyl chitosan, N-alkylidene chitosan, O-sulfonyl chitosan, sulfated chitosan, phosphorylated chitosan, nitrated chitosan, alkalichitin, alkalichitosan, and metal chelates.

* * * * *